United States Patent [19]

Kanda

[11] Patent Number: 5,045,683
[45] Date of Patent: Sep. 3, 1991

[54] LIGHT ABSORPTION DETECTOR WITH LIGHT EMITTING AND LIGHT RECEIVING ELEMENTS

[75] Inventor: Masahiko Kanda, Osaka, Japan

[73] Assignee: Sumitomo Electric Industries, Ltd., Osaka, Japan

[21] Appl. No.: 465,928

[22] Filed: Jan. 16, 1990

[30] Foreign Application Priority Data

Jan. 17, 1989 [JP] Japan .................................. 1-4137[U]
May 10, 1989 [JP] Japan .................................. 1-116757

[51] Int. Cl.$^5$ .............................................. G01J 1/32
[52] U.S. Cl. ................................ 250/205; 250/214 C
[58] Field of Search .................... 250/205, 238, 214 C; 315/151, 158; 372/29, 31

[56] References Cited

U.S. PATENT DOCUMENTS

| | | | |
|---|---|---|---|
| 4,182,977 | 1/1980 | Stricklin, Jr. | 315/158 |
| 4,431,947 | 2/1984 | Ferriss et al. | 315/151 |
| 4,695,714 | 9/1987 | Kimizuka et al. | 250/205 |
| 4,701,607 | 10/1987 | El-Hanany et al. | 250/205 |
| 4,724,314 | 2/1988 | Caimi | 250/205 |
| 4,837,428 | 6/1989 | Takagi et al. | 250/205 |
| 4,917,031 | 4/1990 | Itoh | 250/205 |

FOREIGN PATENT DOCUMENTS

| | | |
|---|---|---|
| 0127947 | 12/1984 | European Pat. Off. . |
| 0247777 | 12/1987 | European Pat. Off. . |
| 2487010 | 1/1982 | France . |
| 60-158803 | 10/1985 | Japan . |

OTHER PUBLICATIONS

Article Entitled "Design Notes" 74, Control and Instrumentation, Jun. 1981, vol. 13, No. 6, London England; p. 17.

*Primary Examiner*—David C. Nelms
*Attorney, Agent, or Firm*—W. G. Fasse; D. H. Kane, Jr.

[57] ABSTRACT

A light absorption detector has one or two light emitting members and a light receiving element spaced a predetermined distance apart from each other on a film substrate (1). Light is transmitted from one side to the other side of a subject. a change in the absorption magnitude of this transmitted light by the subject is then detected to provide respective information. A photodiode (PD) is located near the light emitting member or near two light emitting diodes (LED1, LED2). The photodiode detects a change in the quantity of light emitted. A CPU (16) corrects a change in the quantity of light with a change in the temperature of the light emitting element for controlling the current flowing to the light emitting member or light emitting diodes. Futher, a thermistor (37) and a heater (39) are located in the vicinity of at least one of a light emitting diode (34) and a photodiode (31). A CPU (43) controls a current flowing through the heater in response to a detection of an output of the thermistor so that the temperature of at least of the light emitting member or of the light receiving element is maintained constant.

7 Claims, 6 Drawing Sheets

(a) CHANGE IN TEMPERATURE OF LED

(b) DRIFT IN TEMPERATURE OF LED LUMINOUS POWER (c) SUPPLY CURRENT OF LED (d) LED LUMINOUS POWER

→ TIME

FIG.6

$V_{PD1P} = a \cdot i_{LED1P}$

LIGHT ABSORPTION DETECTOR WITH LIGHT EMITTING AND LIGHT RECEIVING ELEMENTS

FIELD OF THE INVENTION

The present invention relates generally to light absorption detectors, and more particularly to a photosensor for detecting information on a subject such as blood pressure and concentrations of pigments in blood by transmitting light from one side to the other side of a patient and then detecting a change in the magnitude of absorption of light transmitted through a patient's tissue.

BACKGROUND OF THE INVENTION

Such an apparatus has conventionally been known for evaluating the pulse and blood pressure by calculations made after transmitting light through the tissue of a finger tip, detecting a change in the transmittance (reflectance) of light in the blood in the finger and then processing a detection signal thereof. One example of a photosensor employed in this apparatus is disclosed in Japanese Utility Model Laying-Open No. 60-158803.

Figure 11:
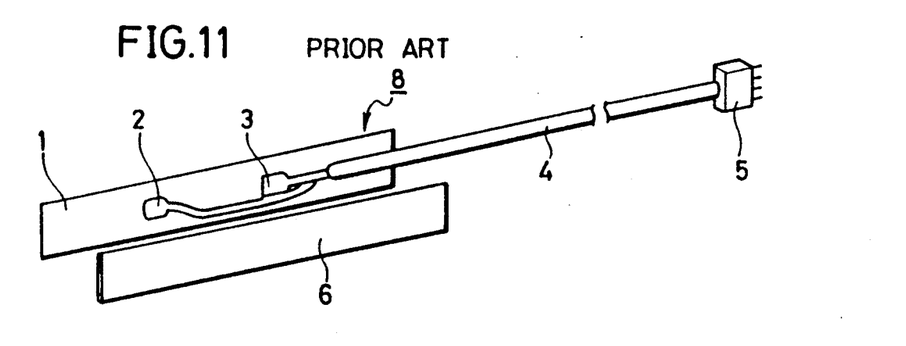
FIG. 11 is a view showing one example of a conventional photosensor.
Figure 12:
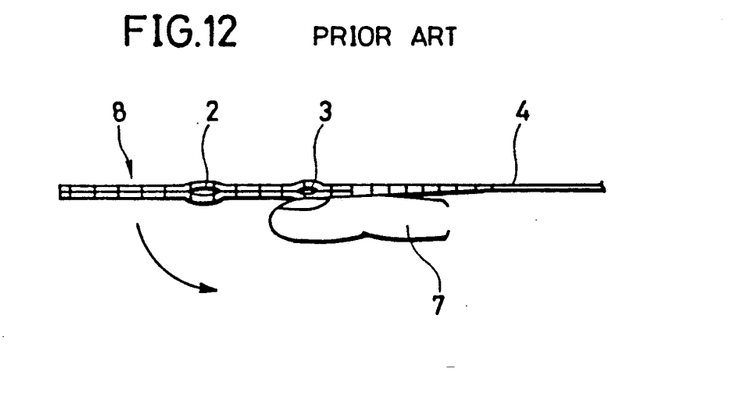
FIG. 12 is a longitudinal section view of the photosensor shown in FIG. 11.
Figure 13:
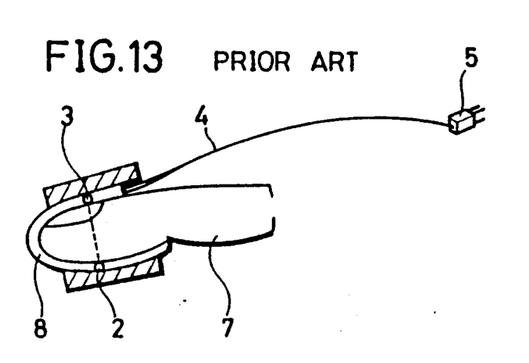
FIG. 13 is a cross sectional view in which the photosensor of FIG. 10 is attached to a finger.
Figure 14:
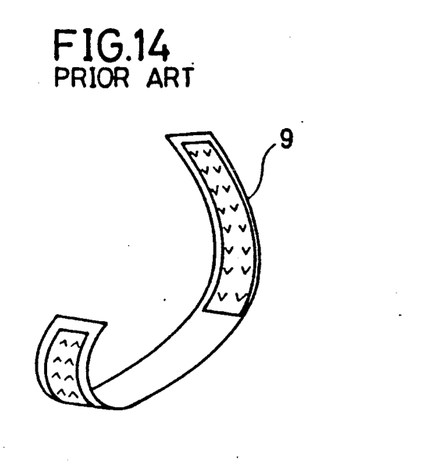
FIG. 14 is a perspective view of an attachment tape for securing the photosensor to a finger.

FIG. 11 is a perspective view of the photosensor disclosed in the above Japanese Utility Model Publication; FIG. 12 is a cross sectional view of the photosensor shown in FIG. 11; FIG. 13 is a cross sectional view showing the photosensor of FIG. 11 attached to a finger; and FIG. 14 is a perspective view of a fixing tape for securing the photosensor to a finger.

First, a conventional photosensor 8 will now be described with reference to FIGS. 11-14. The photosensor 8 shown in FIG. 11 transmits light from one side to the other side of the finger and detect a change in the magnitude of this transmitted light depending on the blood content in the finger. A light emitting element 2 and a light receiving element 3 are spaced a predetermined distance, corresponding to the size of the finger, apart from each other on a flexible film substrate 1. A transparent flexible light transmissive film 6 is attached to the film substrate 1 so as to cover the light emitting and receiving elements 2 and 3.

The usage of the photosensor 8 shown in FIG. 11 will be described with reference to FIGS. 12-14. The photosensor 8 is wound around a finger 7 so that the tip of the finger 7 is sandwiched between the light emitting element 2 and the light receiving element 3, as shown in FIG. 12. The fixing tape 9 shown in FIG. 14 is then wound on the photosensor 8 and around the finger. This fixing tape 9 is rectangular and comprises physical adhesion means on a front surface of its one end and on a reverse surface of the other end. Winding this tape 9 on the photosensor 8 to lap the front surface of one end over the reverse surface of the other end causes the photosensor 8 to be firmly secured to the finger 7. When a power is supplied to conductors 4 through a connector 5 of a signal processing apparatus (not shown), the light emitting element 2 emits light. This emitted light is transmitted through the finger 7 and directed to the light receiving element 3. The light receiving element 3 receives this light and supplies a detection signal to the main body of the signal processing apparatus through the lead 4 and the connector 5. The signal processing apparatus detects a change in the transmittance at this time, processing the detected signal and then performing a calculation to provide a pulse and a blood pressure value.

The light emitting element 2 employed in the above photosensor 8 generally uses a light emitting diode. The light emitting diode is liable to have its output power and the wavelength of emitted light change depending on ambient temperature. In addition, attaching the photosensor 8 onto a living body, e.g. the finger 7 renders the living body ischemic or hemostatic, so that the body temperature of the finger 7 is decreased, or increased due to an increase in blood pressure. Thus, the ambient temperature of the light emitting element 2 changes, and consequently the output power or the luminescence wavelength change. However, the output power or the luminescence wavelength of the light emitting element 2 is required to be kept constant in order to correctly measure a pulse value, a blood pressure value and the like.

SUMMARY OF THE INVENTION

It is an object of the present invention to provide a light absorption detector referred to herein simply as photosensor in which an output power or wavelength of a light emitting element does not change even with a change in ambient temperature.

It is another object of the present invention to provide a photosensor for detecting a change in the quantity of light with a change in the temperature of a light emitting element, controlling current flowing through the light emitting element in response to a detected output thereof and correcting the change in the quantity of light with the change in the temperature of the light emitting element.

It is a further object of the present invention to provide a photosensor in which an output power or wavelength does not change with a light emitting element or ambient temperature of the light emitting element being kept constant, even if the photosensor is attached to a subject.

Briefly, the photosensor or light absorption detector according to the present invention emits light to a subject, receives light from the subject and detects the magnitude of absorption of light by the subject. In this photosensor, a light emitting element which directs light to the subject is provided on a film substrate; a first light receiving element is spaced, on the film substrate, a predetermined distance apart from the light emitting element; and a second light receiving element is provided near the light emitting element. Current flowing through the light emitting element is controlled so as to correct a change in the quantity of light with a change in the temperature of the light emitting element in response to the power of received light of the second light receiving element.

Therefore, in accordance with the present invention, the light emitting element or the temperature of the light emitting element can be kept constant independently of a change in the temperature of the subject. This enables the output power or wavelength of the light emitting element to be kept constant, thereby obtaining correct information on the subject.

According to another aspect of the present invention, a heater and a temperature sensor are provided near at least either one of the light emitting element and the light receiving element, and the vicinity of either the light emitting element or the light receiving element is heated by such a heater so that a detected temperature is maintained constant.

Therefore, also in this aspect, the temperature of the light emitting element or the light receiving element can be kept constant independently of the subject's changing temperature so that the output power or wavelength of the light emitting element is kept constant, and thus correct subject information is obtained.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 8A to 8C are views showing a second embodiment of the present invention; specifically.

FIGS. 9A and 9B are views showing an example in which a thermistor is provided in a heat sink of the light emitting diode; specifically.

DESCRIPTION OF THE PREFERRED EMBODIMENTS

Figure 1A:
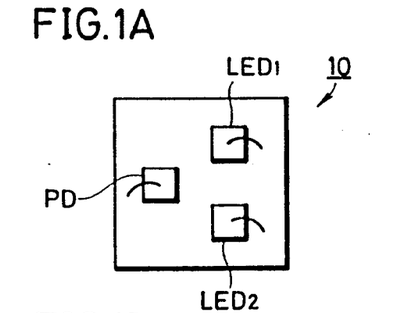
FIGS. 1A and 1B show one example of an arrangement of light emitting diodes and a photodetector on a substrate in a first embodiment of the present invention.
Figure 1B:
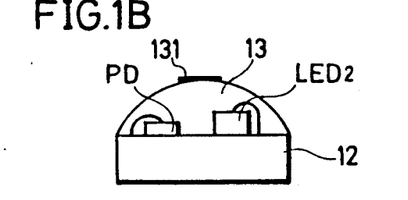

FIG. 1A is a plan view of one example of light emitting diodes and a photodetector in one arrangement of an embodiment of the present invention, and FIG. 1B is a side view thereof. Referring to FIGS. 1A and 1B, a light emitting diode device 10 substitutes for the light emitting element 2 of the conventional photosensor 8 shown in FIG. 10. Two LED chips $LED_1$ and $LED_2$ are provided on a substrate 12, and a photodiode PD is provided near these LED chips $LED_1$ and $LED_2$. The photodiode PD directly receives light from the LED chips $LED_1$ and $LED_2$. The LED chips $LED_1$ and $LED_2$ usually radiate light also to portions beneath a p-n junction plane, and this radiated light is received by the photodiode PD acting as a photo detector.

The photodiode PD detects a change in the quantity of light from the LED chips $LED_1$ and $LED_2$ in accordance with a change in the ambient temperature. Transparent epoxy resin 13 is applied onto the substrate 12 so as to cover these LED chips $LED_1$ and $LED_2$ and the photodiode PD. The epoxy resin may be replaced by transparent polyester resin. The photodiode PD may be provided at a position where light radiated from the LED chips $LED_1$ and $LED_2$ can reflect on an inner surface of the semi-spherical epoxy resin 13 to be received by the photodiode PD. Further, the following process may be employed as shown in FIG. 1B. An Ag film 131 on which Ag is evaporated is formed on a portion of the surface of the epoxy resin 13. The light radiated from the LED chips $LED_1$ and $LED_2$ is then positively and partially reflected at the Ag film 131, and this reflected light is detected by the photodiode PD.

Figure 2:
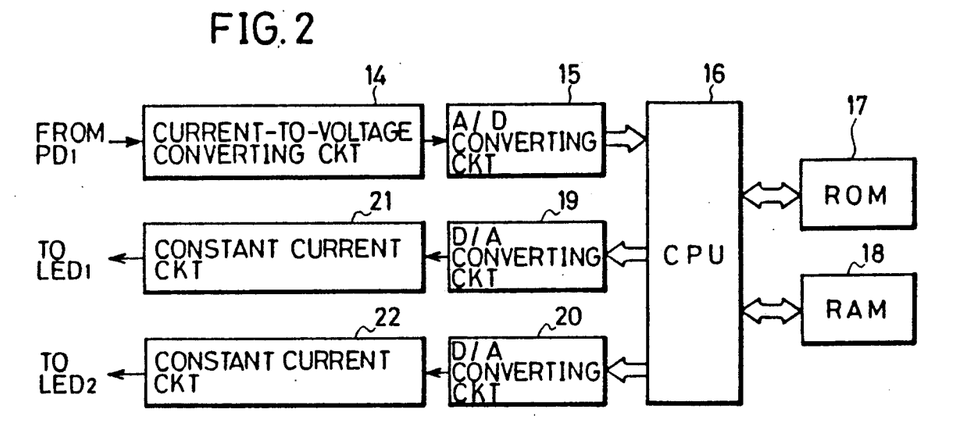
FIG. 2 is a schematic block diagram of one embodiment of the present invention.
Figure 3:
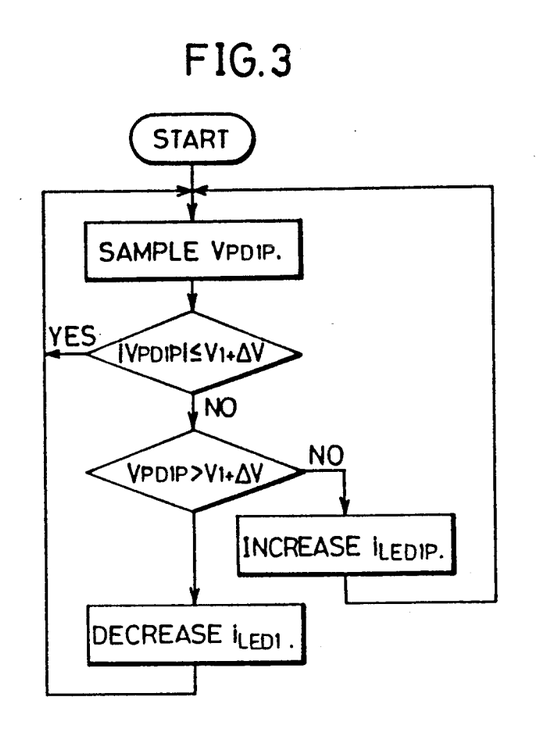
FIG. 3 is a flow chart drawn for describing an operation of one embodiment of the present invention.

FIG. 2 is a schematic block diagram of the first embodiment of the present invention. Referring to FIG. 2, power generated by light received by the photodiode PD shown in FIGS. 1A and 1B, is supplied to a current-to-voltage converting circuit 14. Current flowing through the photodiode PD is then converted into voltage, and this voltage is supplied to an A/D converting circuit 14. An A/D converting circuit 15 converts a voltage value into a digital value and then supplies the digital value to a CPU 16. The CPU 16 is connected to a ROM 17 and a RAM 18. As shown in FIG. 3 which will be described later, a program for correcting the change in the quantity of light of the LED chips $LED_1$ and $LED_2$ with the change in temperature, has been stored in the ROM 17. The CPU 16 supplies a current value flowing through the LED chips $LED_1$ and $LED_2$, as a digital signal, to D/A converting circuits 19 and 20. The D/A converting circuits 19 and 20 convert a digital value as the current value into an analog value and supply this analog value to constant current circuits 21 and 22. The constant current circuit 21 supplies a current to the LED chip $LED_1$, while the constant current circuit 22 supplies a current to the LED chip $LED_2$.

Figure 4:
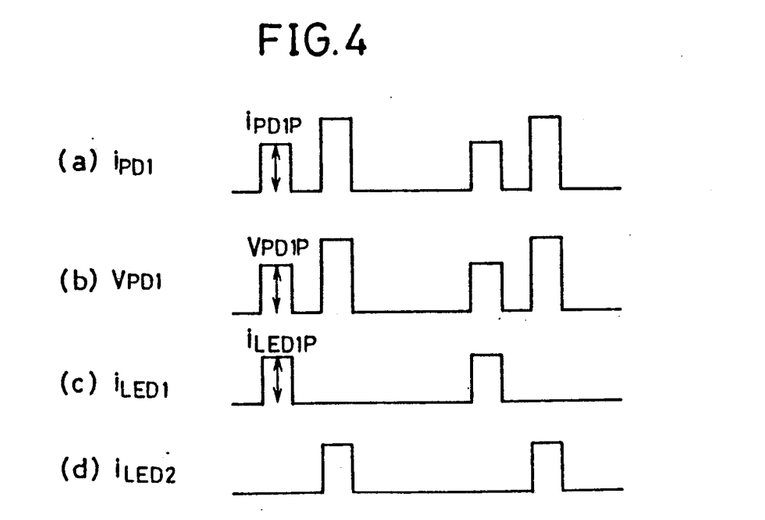
FIG. 4 is a timing chart for describing the operation of one embodiment of the present invention.
Figure 5:
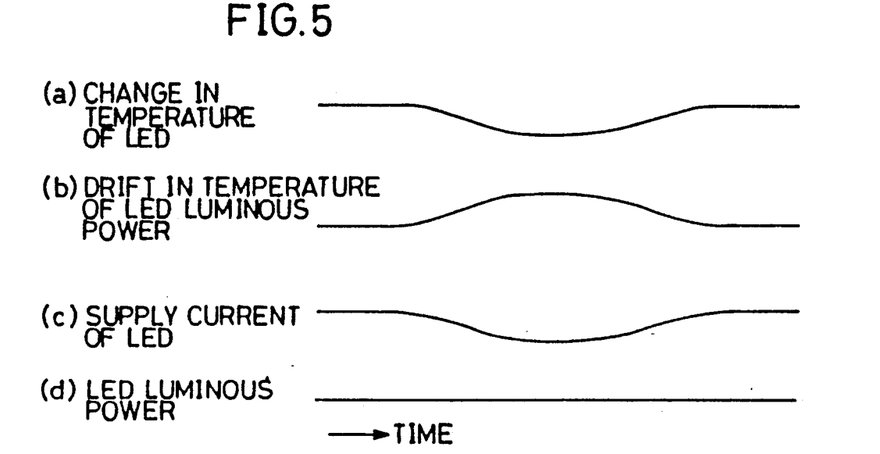
FIG. 5 is a diagram showing changes in the power of emitted light due to a change in the temperature of the light emitting diode as a function of time.
Figure 6:
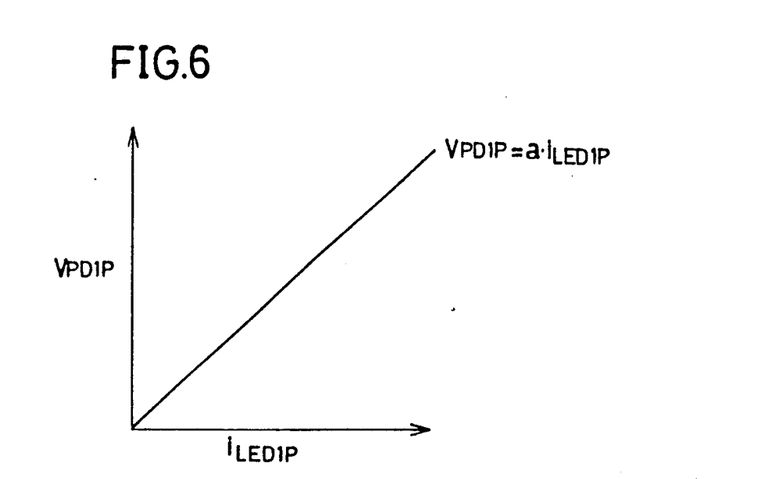
FIG. 6 is a characteristic view showing the relationship between a current flowing through the light emitting diode and an output voltage of a photodiode.

FIG. 3 is a flow chart drawn for the description of a detailed operation of one embodiment of the present invention; FIG. 4 is a timing chart therefor; FIG. 5 shows a change in the power of emitted light of the light emitting diode due to a change in the temperature thereof; FIG. 6 is a characteristic diagram showing the relationship between a current flowing through the light emitting diode and an output voltage of the photodiode; and FIG. 7 shows a relative light output as a function of different temperature characteristics of the light emitting diodes $LED_1$, $LED_2$.

Referring to FIGS. 1A-7, the detailed operation of one embodiment of the present invention will now be described. Since each of the LED chips $LED_1$ and $LED_2$ operates in a similar manner, only the operation of the LED chip $LED_1$ will be described. An output current $i_{PD1P}$ of the photodiode PD receiving light shown in FIG. 4 (a) is supplied to the current-to-voltage converting circuit 14 to be converted into a voltage $V_{PD1P}$, as shown in FIG. 4 (b). This converted voltage is then further converted into a digital signal by the A/D converting circuit 15 which supplies the digital signal to the CPU 16. The CPU 16 samples the output voltage $V_{PD1P}$ of the photodiode PD to determine if this output voltage $V_{PD1P}$ is lower than a predetermined output voltage $V_1$ of the photodiode PD and lower than an allowable voltage $\Delta V_1$ thereof. If the output voltage $V_{PD1P}$ is determined as $V_{PD1P} > V_1 + \Delta V_1$, the CPU 16 increases or decreases a value of a current $i_{LED1}$ flowing through the LED chip $LED_1$.

In this case, the relationship of $V_{PD1P} = a \cdot i_{LED1P}$ at a specific temperature may be obtained with respect to the characteristic of $V_{PD1P}$ as a function of $i_{LED1P}$ shown in FIG. 6 to increase or decrease the value of the current $i_{LED1}$ by the value of $|V_{PD1P}-V|/a$. The specific temperature in this case is preferably selected in the range of 35° C.-38° C. close to by body temperature of a human body.

Figure 7:
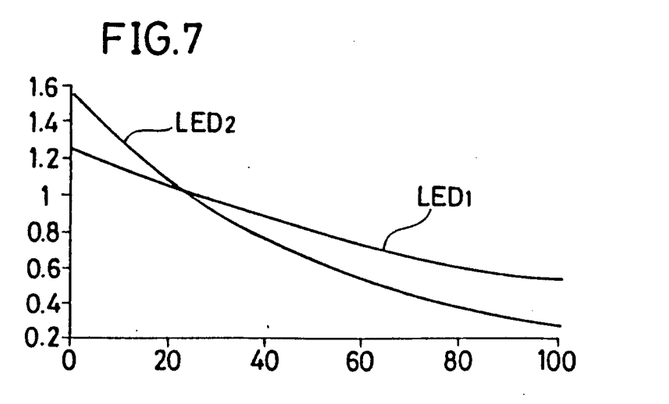
FIG. 7 is a graph showing a relative light output of the light emitting diode as a function of temperature.

In general, the power of emitted light of the light emitting diode 10 increases with a decreasing temperature or decreases with an increasing temperature, as shown in FIG. 7. Thus, when the temperature decreases as shown in FIG. 5 (a), the power of emitted light of the light emitting diode 10 increases as shown in FIG. 5 (b). However, decreasing a supply current i of the light emitting diode 10 to offset this increased amount of the emitted light power (FIG. 5 (c)) enables the emitted light power to approximately be constant and thus enables a correction of a fluctuation in the emitted light power with a change in the temperature, as shown in FIG. 5 (d) as a function of time.

Figure 8A:
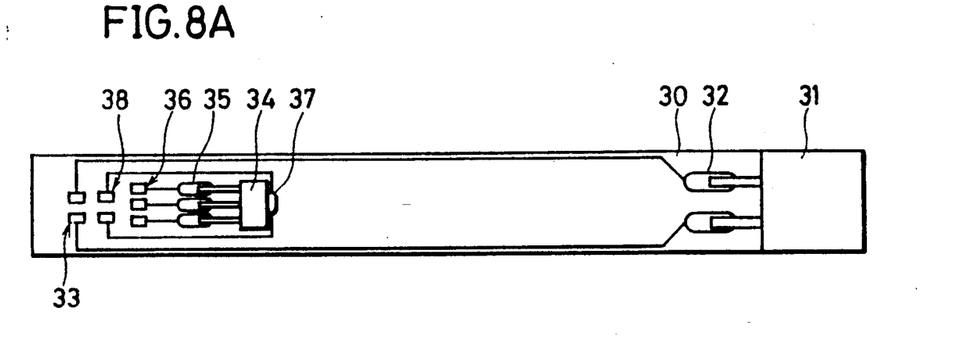
FIG. 8A is a plan view of the second embodiment.
Figure 8B:
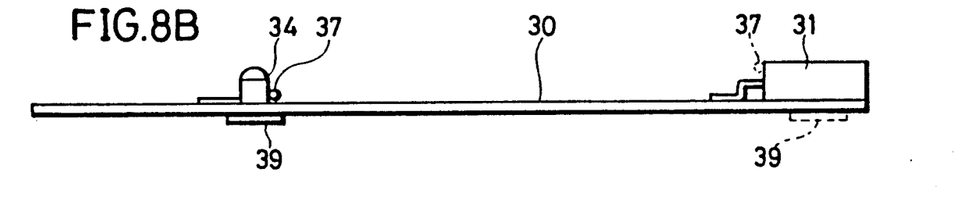
FIG. 8B is a side view thereof.
Figure 8C:
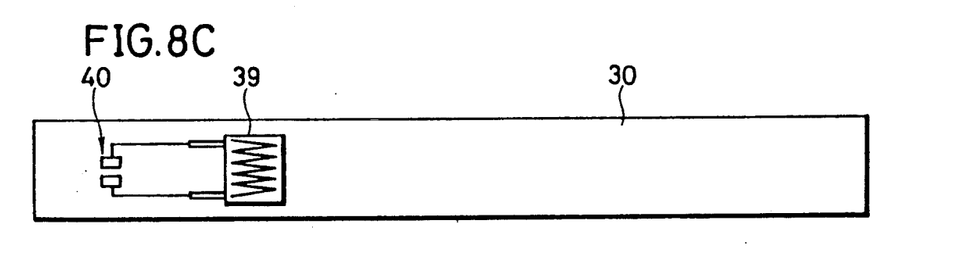
FIG. 8C is a bottom view.

FIGS. 8A to 8C show another embodiment of the present invention; specifically, FIG. 8A is a plan view, FIG. 8B is a side view and FIG. 8C is a bottom view.

The construction of this embodiment of the present invention will now be described with reference to FIGS. 8A to 8C. A photodiode 31 as one example of the light receiving element is provided at one end of the surface of a film substrate 30. Lead terminals of the photodiode 31 are soldered onto patterns 32 formed on the film substrate 30. A light emitting diode 34 as one example of the light emitting element is provided at the other end of the surface of the film substrate 30. Lead terminals of the light emitting diode 34 are soldered onto patterns 35 formed on the film substrate 30. A thermistor 37 as one example of temperature detecting means is provided near the light emitting diode 34. Patterns 33, 36 and 38 for connecting cables are formed on the left side of the pattern 35. The patterns 33 and the patterns 32 are for the photodiode 31, the patterns 36 and the patterns 35 are for the light emitting diode 34, and the patterns 38 are for the thermistor 37. The patterns are electrically connected through linear conductors as shown.

A heater 39 as one example of heating means is provided at a position, corresponding to the light emitting diode 34, on the reverse surface of the film substrate 30. This heater 39 comprises a nichrome resistor thinly formed, for example. Terminals of the heater 39 are electrically connected to patterns 40.

In the photosensor constructed as above, a main body of a processing apparatus shown in FIG. 10, which will be described later, is connected through a cable (not shown) to the patterns 36 for the light emitting diode 34, the patterns 38 for the thermistor 37, the patterns 33 for the photodiode 31 and the patterns 40 for the heater 39.

Figure 9A:
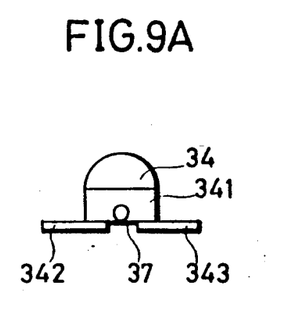
FIG. 9A is a side view.
Figure 9B:
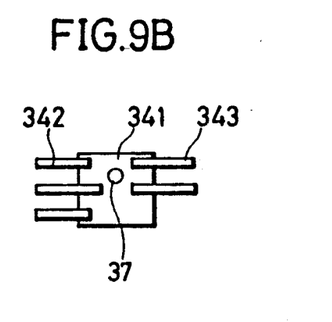
FIG. 9B is a bottom view.

FIGS. 9A and 9B show an example in which the thermistor 37 is located in a heat sink 341 of the light emitting diode 34. Terminals 342 for the light emitting diode 34 and terminals 343 for the thermistor 37 are attached to the heat sink 341.

While the above embodiment shows the example in which the thermistor 37 is provided near the light emitting diode 34, the thermistor 37 and the heater 39 may be located near the photodiode 31, as shown by the dotted line of FIG. 8B, in relation to ambient temperature of the photodiode 31.

Figure 10:
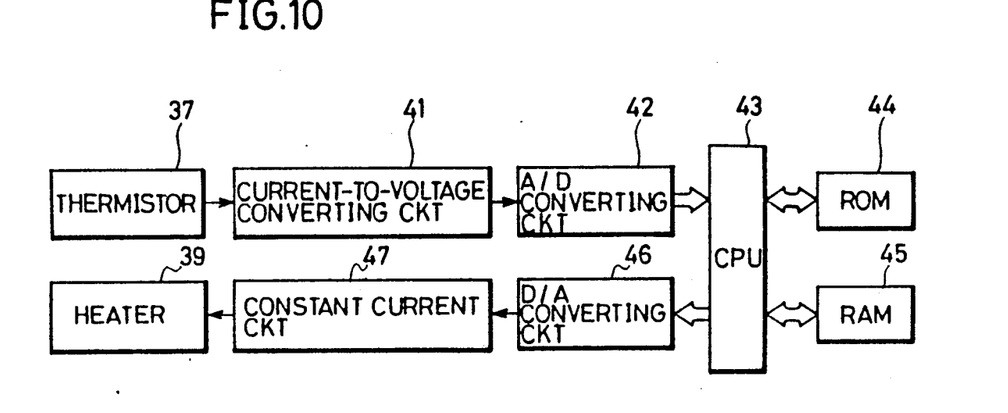
FIG. 10 is a schematic block diagram of a third embodiment of the present invention.

FIG. 10 is a schematic block diagram for illustrating the operation of the detector according to the above described second embodiment of the present invention.

A temperature detecting signal of the thermistor 37 shown in FIG. 8A is applied to a current-voltage converting circuit 41 to for conversion into a voltage which is further converted into a digital signal by an A/D converting circuit 42 the output of which is applied to a CPU 43. The CPU 43 is connected to a ROM 44 and RAM 45. The ROM 44 has stored therein a program for controlling the heater 39 in response to a temperature detected by the thermistor 37 so that the ambient temperature of the light emitting diode 34 shown in FIG. 8A is maintained constant. The RAM 45 stores data of the temperature detected by the thermistor 37. The CPU 43 supplies data of a current, which is to flow through the heater 39, to a D/A converting circuit 46 in response to the digital signal representing the detected temperature, which is supplied from the A/D converting circuit 42, in accordance with the program stored in the ROM 44. The D/A converting circuit 46 converts the digital signal into an analog signal, so that a current is supplied from a constant current circuit 47 to the heater 39.

As has been described above, according to this embodiment, since the thermistor 37 and the heater 39 are located near at least either one of the light emitting diode 34 and the photodiode 31 so that the vicinity of at least one of the light emitting diode 34 and the photodiode 31 is heated by the heater 37 to make the detected temperature constant, the temperature of the light emitting diode 34 or that of the photodiode 31 is kept constant independently of the change in the temperature of the subject. Consequently, it becomes possible to keep the output power and wavelength of the light emitting element constant and thus obtain correct subject information.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A light absorption detector, comprising:
a film substrate light emitting means ($LED_1$, $LED_2$) secured on a flat surface of said film substrate for directing light to a subject; a first light receiving element spaced, on said film substrate, a predetermined distance apart from said light emitting means, for receiving light from said subject; a second light receiving element located near said light emitting means, for detecting a change in the quantity of light with a change in the temperature of said light emitting means; said second light receiving element being arranged together with said light emitting means on the same flat surface of said film substrate for directly receiving light from said light emitting means; control means (14, 15, 16) for controlling a current flowing through said light emitting element so as to correct the change in the quantity of light with the change in the temperature of said light emitting element in accordance with a power of received light of said second light receiving element; said detector further comprising a transparent semispherical resin cover (13) on said film substrate for covering said light emitting means and said second light receiving element, said second light receiving element being positioned for receiving a portion of light received from said light emitting means and reflected by a semi-spherical inner surface of said resin cover (13); and wherein said resin cover (13) comprises an evaporated silver film (131) on its surface.

2. The light absorption detector in accordance with claim 1, wherein said light emitting means comprise two LED chips (LED1, LED2) each located at an equal distance apart from said second light receiving element and at different positions.

3. The light absorption detector in accordance with claim 1, wherein said control means comprise a current-to-voltage converting circuit (14) for converting a current of said second light receiving element into a voltage; and A/D converting circuit (15) for converting the voltage converted by said current-to-voltage converting circuit into a digital signal; and a central processing circuit (16) responsive to the digital signal converted by said A/D converting circuit for determining whether an output voltage of said second light receiving element is lower than a predetermined voltage for controlling a current flowing through said light emitting means.

4. The light absorption detector of claim 1, wherein said light emitting means comprise at least two light emitting diode chips having different temperature characteristics.

5. A light absorption detector, comprising: a film substrate; a light emitting means (34) located on one major surface of said film substrate for directing light through a subject; a light receiving element (31) spaced, on said one major surface of said film substrate, a predetermined distance apart from said light emitting means, for receiving light transmitted through said subject; heating means (39) located on the other main surface of said film substrate substantially opposite said light emitting means; temperature detecting means (37) arranged in the vicinity of at least one of said light emitting means and said light receiving element; and control means (43) for making said heating means heat the vicinity of at least one of said light emitting element and said light receiving element so as to keep a temperature detected by said temperature detecting means constant.

6. The light absorption detector in accordance with claim 5, wherein said light emitting means comprises a heat sink (341), and wherein said temperature detecting means is located in said heat sink.

7. A light absorption detector, comprising: a film substrate; a light emitting means (34) located on one major surface of said film substrate for directing light through a subject; a light receiving element (31) spaced, on said one major surface of said film substrate, a predetermined distance apart from said light emitting means, for receiving light transmitted through said subject; heating means (39) located on the other main surface of said film substrate substantially opposite said light receiving element; temperature detecting means (37) arranged in the vicinity of at least one of said light emitting means and said light receiving element; and control means (43) for making said heating means heat the vicinity of at least one of said light emitting element and said light receiving element so as to keep a temperature detected by said temperature detecting means constant.

* * * * *